United States Patent [19]
Matsuo et al.

[11] Patent Number: 4,664,520
[45] Date of Patent: May 12, 1987

[54] CAMERA FOR VISUAL INSPECTION

[75] Inventors: Junichi Matsuo, Chita; Sadanari Muto, Kasugai, both of Japan

[73] Assignee: NGK Insulators, Ltd., Japan

[21] Appl. No.: 776,892

[22] Filed: Sep. 17, 1985

[30] Foreign Application Priority Data

| Sep. 29, 1984 | [JP] | Japan | 59-148094[U] |
| Feb. 1, 1985 | [JP] | Japan | 60-14048[U] |
| Feb. 1, 1985 | [JP] | Japan | 60-14049[U] |
| Apr. 19, 1985 | [JP] | Japan | 60-59355[U] |

[51] Int. Cl.$^4$ .................. G01N 1/04; G01N 21/88
[52] U.S. Cl. .................................. 356/237; 250/563
[58] Field of Search ............... 356/237, 238, 239, 240, 356/241; 250/562, 563

[56] References Cited

PUBLICATIONS

C. B. Haehner, Inspection System for Round Objects Western Electric Tech. Digest 6, Apr. 1967, pp. 29–30.

*Primary Examiner*—Gene Wan
*Attorney, Agent, or Firm*—Parkhurst & Oliff

[57] ABSTRACT

A camera for visual inspection of defect on an object having a complicated shape is disclosed. This camera is provided with a reflecting mirror having two symmetrical reflecting surfaces to split incident light into two portions and direct them onto two linear image sensing devices mounted on inner surface of the camera body at separate positions. The received lights are converted into electric signals and after processing to obtain a difference signal, a signal indicating presence of a defect is obtained remarkably.

5 Claims, 17 Drawing Figures

FIG_5
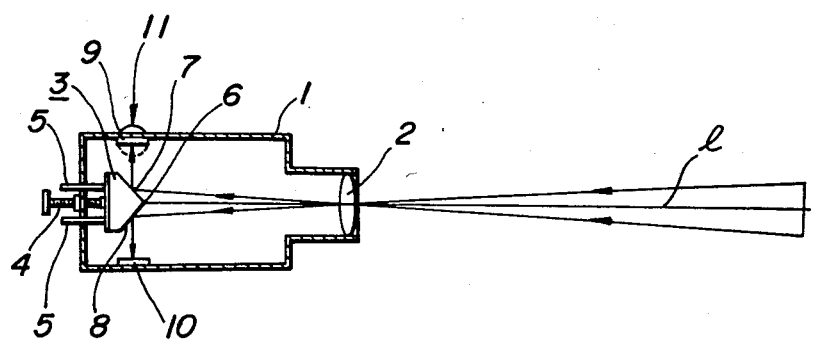
FIG_6
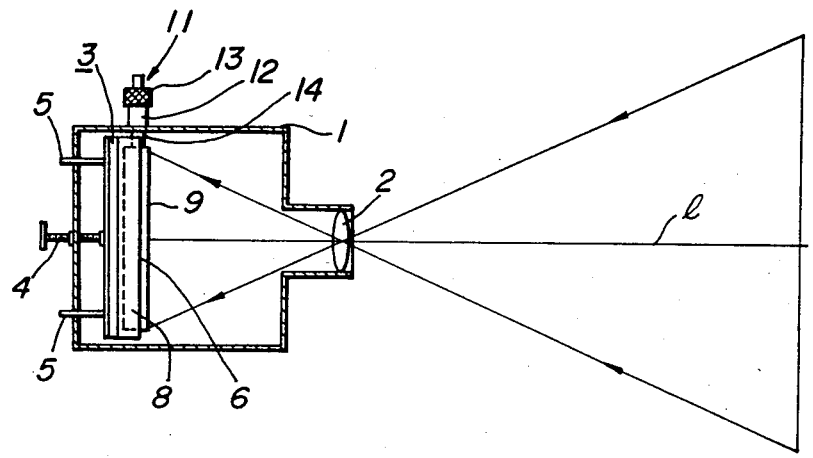

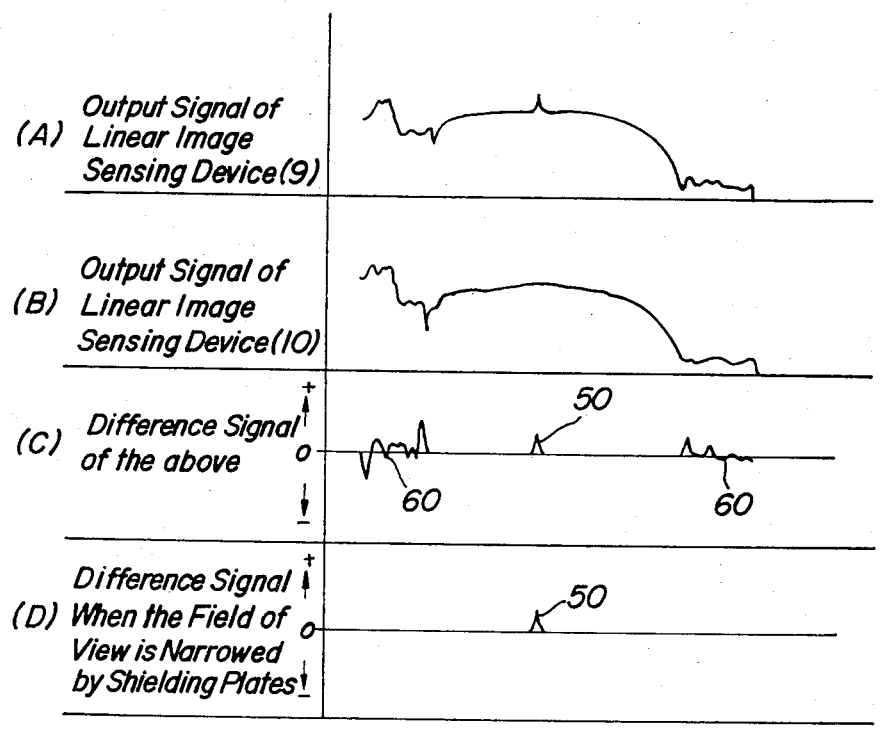

CAMERA FOR VISUAL INSPECTION

BACKGROUND OF THE INVENTION (1) Field of the Invention

The present invention relates to a camera for visual inspection to be used for optically inspecting presence of surface defects on an object having a complicated outer configuration.

(2) Related Art Statement

A conventional camera for visual inspection used for checking defects on a sheet shape body, such as a glass sheet or a steel sheet, comprises a linear image sensor having a plurality of sensor elements arranged linearly on an optic axis of the lens of the camera. However, as this kind of the camera for visual inspection is to convert the brightness of the surface of an object directly into an electric signal, it has an essential disadvantage in that the device can not identify the brightness variation due to presence of defect from the brightness variation caused from uneven illumination when the device is used for an object having a complicated rugged surface such as an insulator. In one method for improving the aforementioned disadvantage, a visual sensor system is possible to be considered, in which two linear image sensing devices are closely arranged on the focus plane of a camera in parallel direction to the plane and the influence of the uneven illumination is cancelled by applying operation to take difference between the output signals derived from the two linear image sensing devices.

However, a conventional linear image sensing devce is usually equipped with a transfer gate and a shift register around the light receiving portion so that it can not be arranged very closely less than a certain distance of an order of about 10 mm since the overall width of the device is already about an order of 10 mm. If the magnification of the lens is assumed as M, the device is to be arranged to compare the brightness on lines apart from 10×M mm each other on the surface of the object. Accordingly, it has been turned out that the measuring accuracy can not be improved over a certain value. Although the linear image sensing device is manufactured under a condition of very strict quality control, the light sensitivity may vary in a range of a few percent along the direction of array of the sensor elements. So there is a problem of deterioration of the inspection accuracy when two linear image sensing devices having different sensitivity characteristics are used.

Furthermore, for inspecting all the outer surface of an object having a complicated and rugged surface configuration such as an insulator, it is necessary to use a plurality of cameras as shown in FIG. 16. In this case, the required field of view for each one of the cameras varies greatly so that if cameras having a same view angle are used, the distance between the camera and the object must be varied for camera by camera and hence the magnification of the camera varies which results a problem of causing variation of the inspection accuracy. If the number of cameras are arranged at a certain constant distance from the object, there will be a case in which a portion of the surface other than the desired inspecting surface is included in the field of view of a camera as shown by the dotted lines in FIG. 16. It has been turned out that an accurate inspection is not possible in such case since some spurious noise waveforms just like the defect signals appear at both extremities of the field of view of the camera as can be seen from lines (A) to (C) in FIG. 17.

SUMMARY OF THE INVENTION

The present invention is to mitigate the abovementioned problems in the conventional inspection system. The invention has its object to realize a camera for the visual inspection for defects on the surface of an object by using conventional linear image sensing devices and to achieve the comparison of brightness on two closed lines on the surface of the object. The present invention is characterized in that the provision of a reflecting mirror having two symmetrical reflecting surfaces extending in equiangular relationship about the optic axis of the lens of the camera forming a vertex line at the crossing thereof which also extending normal to said optic axis and that two linear image sensing devices are arranged at two separate points on the inner surface of the camera to receive the reflected lights reflected from said two reflecting surfaces.

The invention is further characterized in that a fine adjustment mechanism for adjusting the mount of the linear image sensing device in the direction of array of the sensor elements is provided at least for one of the linear image sensing devices, that a light amount adjusting filter having darkness distribution corresponding to the variation pattern of the sensitivity characteristics along the direction of array of the sensor elements of the linear image sensing device is provided at front of at least one of the devices, and that shielding plates arranged movable toward each other in the direction of array of the sensor elements are provided in front of and in close proximity of each of the linear image sensing devices.

BRIEF DESCRIPTION OF THE DRAWING

FIG. 5 is a horizontal cross-sectional view of an embodiment attached with a fine adjustment mechanism for moving the mount of the linear image sensing device;

FIG. 6 is a vertical cross-sectional view thereof;

FIG. 17 is a waveform diagrams of the output signal and the difference signal of respective image sensing devices wherein the light shielding plates are arranged in front of the linear image sensing device.

DESCRIPTION OF THE PREFERRED EMBODIMENT

The invention will now be explained more fully by referring to the accompanying drawings.

Figure 1:
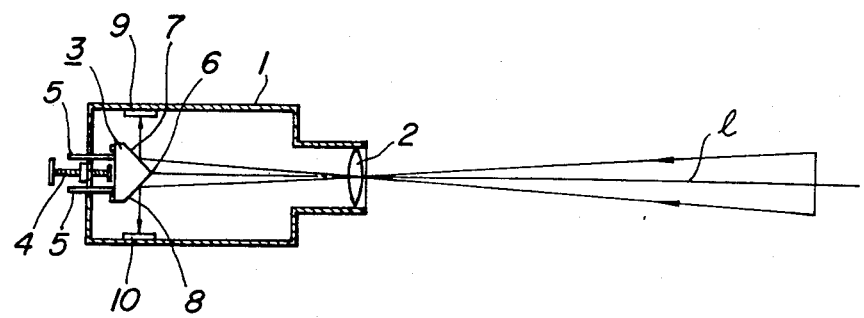
FIG. 1 is a horizontal cross-sectional view showing a first embodiment of the invention.
Figure 2:
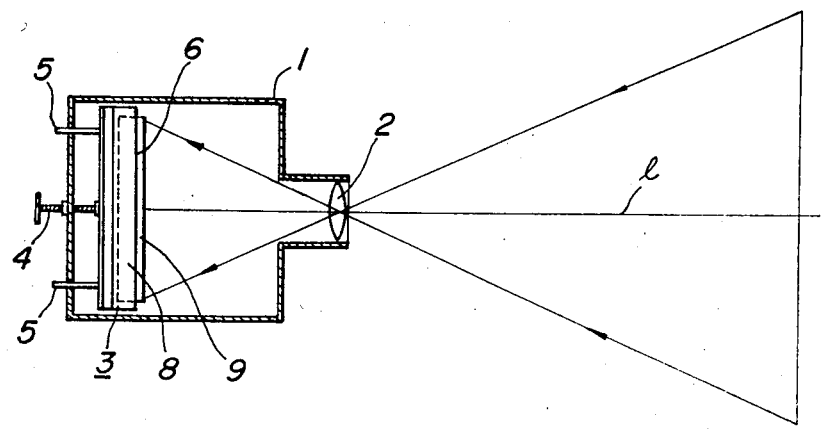
FIG. 2 is a vertical cross-sectional view of the same.

Referring to FIGS. 1 and 2, the camera body 1 for the visual inspection comprises lens 2 having optic axis l. The camera body 1 further comprises a reflecting mirror 3 having pentagonal column shape and of which vertex line being arranged on the optic axis l normal thereto and in a manner freely movable back and forth along the optic axis by means of a driving screw 4 and guide members 5. This reflecting mirror 3 has two reflecting surfaces 7 and 8 extending symmetrically from the vertex line 6 and at equal inclined angle of 45° with respect to the optic axis. Two linear image sensing devices 9 and 10 are arranged on the inner surface of the camera body 1 at locations onto which the reflected lights from the reflecting surfaces 7 and 8 impinge, respectively.

Figure 3:
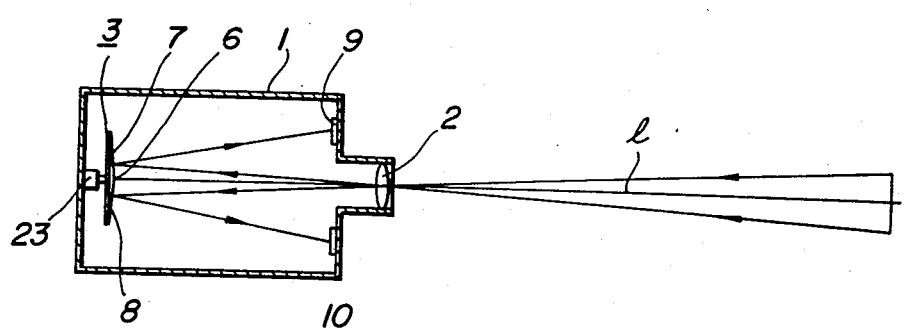
FIG. 3 is a horizontal cross-sectional view showing a second embodiment of the invention.
Figure 4:
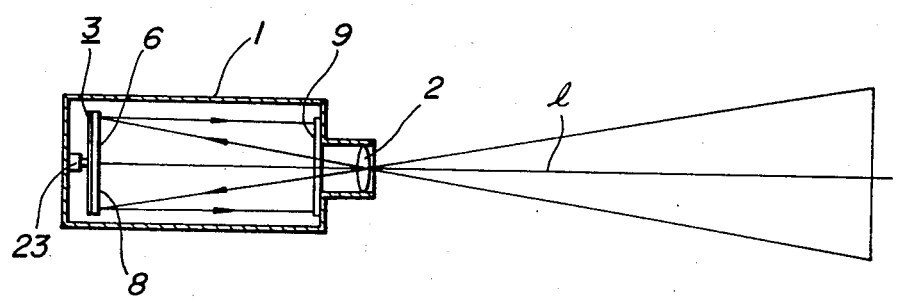
FIG. 4 is a vertical cross-sectional view of the same.

FIGS. 3 and 4 show a second embodiment of the present invention. This embodiment has almost the same construction with the first embodiment. But the symmetrical angle between the reflecting surfaces 7 and 8 of the reflecting mirror 3 with respect to the optic axis l of the lens 2 is selected to be about 85° and the linear image sensing devices 9 and 10 are arranged at front inner side of the camera body 1. In this second embodiment, the reflecting mirror 3 is attached with a piezoelectric (PZT) actuator 23 by which the reflecting mirror 3 is moved along the optic axis l in order to improve the accuracy of the back and forth movement.

In a further embodiment shown in FIGS. 5 and 6, a fine adjustment mechanism 11 is provided for at least one of the two linear image sensing devices for adjusting the mounting location of the sensor element in the direction of array of the sensor elements. The fine adjustment mechanism 11 is just like the driving mechanism of a micro-meter and its outer sleeve 12 is fixed on the outer wall of the camera body 1 and the said one linear image sensing device 9 is attached on the top of a spindle 14 arranged to move at accuracy of order of 10 μm by a rotation of a thimble 13. In this embodiment, a driving mechanism of a micro-meter type is used for the fine adjustment mechanism 11. But the invention is not limited to the illustrated embodiment only. In this embodiment, the other one of the linear image sensing device 10 is assumed to be fixed on the inner surface of the camera body 1, but it is obvious that the both linear image sensing devices 9 and 10 may be provided with the same kind of fine adjustment mechanisms 11.

Figure 15:
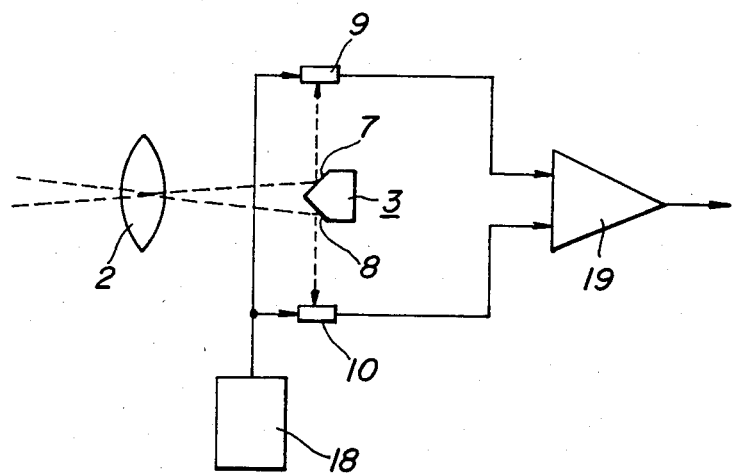
FIG. 15 is a block diagram for showing the overall system of the same.

The linear image sensing devices 9 and 10 are excited simultaneously from a single clock pulse generator 18 provided in a controlling circuit such as shown in FIG. 15. The electric signals derived from the respective sensor elements of the sensing devices 9 and 10 are applied to a differential operation processor 19 simultaneously and a difference signal is derived therefrom.

Figure 10:
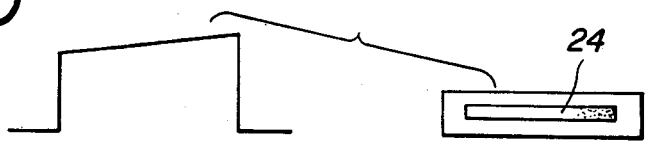
FIGS. 10, 11 and 12 are diagrams for showing variation in the pattern of sensitivity characteristics of the linear image sensing device together with simplified diagram of the corresponding light adjusting filters.
Figure 11:
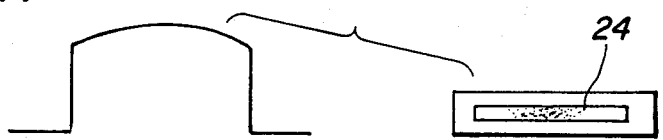
Figure 12:
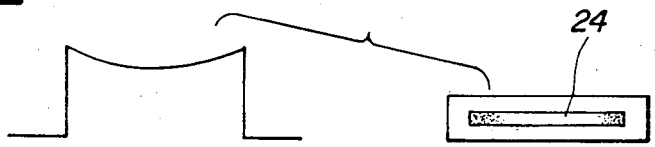

As has been mentioned in the foregoing, the linear imge sensing devices 9 and 10 may vary their optical sensitivity along the direction of array of the sensor elements. In order to compensate unevenness of the sensitivity characteristics due to this variation, a light amount adjusting filter 24, as shown in FIGS. 10 to 12, is arranged in front of at least one of the linear image sensing devices according to the present invention. By the experience of the inventors, the variation patterns of the sensitivity characteristics of almost all the presently available linear image sensing devices may be classified into 3 types. The first one of which is as shown in FIG. 10, in which the characteristic curve ascends from one end towards the other end linearly. The second one is as shown in FIG. 11, in which the both ends are lowered, and the third one is as shown in FIG. 12, which the curve is bent downwardly at the middle. Accordingly, by providing 3 kinds of light amount adjusting filters 24 having complemental darkness distribution with respect to the respective variation pattern of the light sensitivity as shown on the right hand side in the above FIGS. 10 to 12 and by selecting a suitable filter 24 having the absorption distribution to match with the variation pattern of the sensitivity characteristics of the linear image sensing devices, the light sensitivity of the linear image sensing devices 9 and 10 can be made substantially equal along the whole length thereof.

Figure 7:
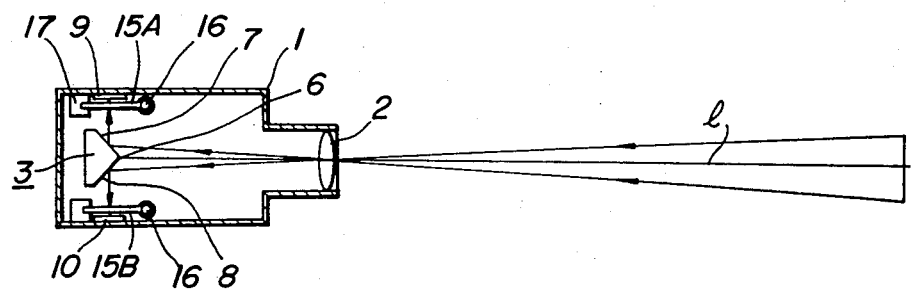
FIG. 7 is a horizontal cross-sectional view showing an embodiment in which light shielding plates are arranged in front of the linear image sensing device.
Figure 8:
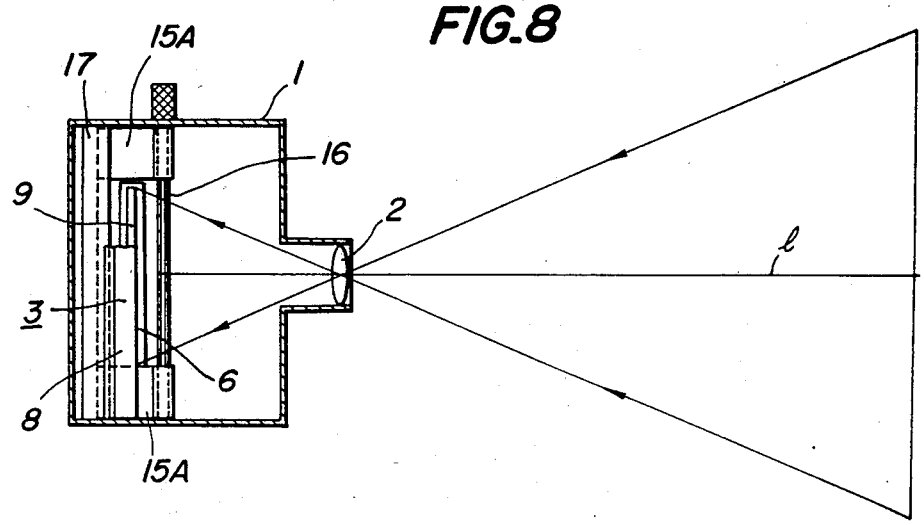
FIG. 8 is a vertical cross-sectional view thereof.
Figure 9:
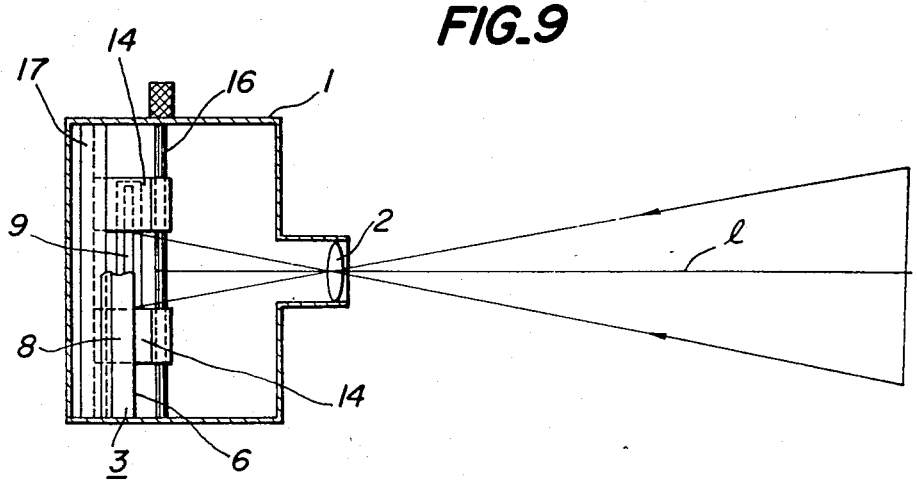
FIG. 9 is also the same vertical cross-sectional view thereof but the field of view is made narrower than that of FIG. 8.

In a further embodiment shown in FIGS. 7 to 9, shielding plates 15A and 15B are arranged at very close proximity in front of the linear image sensing devices 9 and 10, respectively, in a movable manner towards each other in the direction of arrangement of the sensor elements. As can be seen more clearly from FIG. 8, the shielding plates for the linear image sensing device 9 consist from a pair of plates both designated as 15A. Namely a pair of shielding plates 15A and 15A are arranged at locations upper side and lower side in the vertical cross-sectional view. The base end portions of the shielding plates are supported by a driving screw 16 extending along the direction of arrangement of the sensor elements and the other free end portions are supported in a vertical groove of a column member 17 in a manner to allow free sliding movement. In the present invention, which is particularly shown in FIG. 8, a driving screw 16 is provided with opposite direction screws for the upper half and lower half portions so that the pair of shielding plates 15A and 15A may simultaneously be moved equal amount in a direction opposite to each other. The two driving screws 16 and 16 located at both sides of the optical axis l may be coupled by means of for instance belts, chain, etc., so as to move the both pairs of shielding plates 15A, 15A and 15B, 15B simultaneously. The upper shielding plate and the lower shielding plate may also be arranged to be driven to move independently.

By adjustment of the shielding plates, the field of view of the respective linear image sensing device 9 or 10 may be varied selectively. In this case, if the distance between the shielding plates and the linear image sensing device becomes larger, the image at boundaries may become unclear. Therefore, it is better to arrange the shielding plates 15A and 15B located at front of the linear image sensing devices 9 and 10 as close as possible thereto.

The function of the inventive camera for visual inspection will be explained hereinafter.

Figure 13:
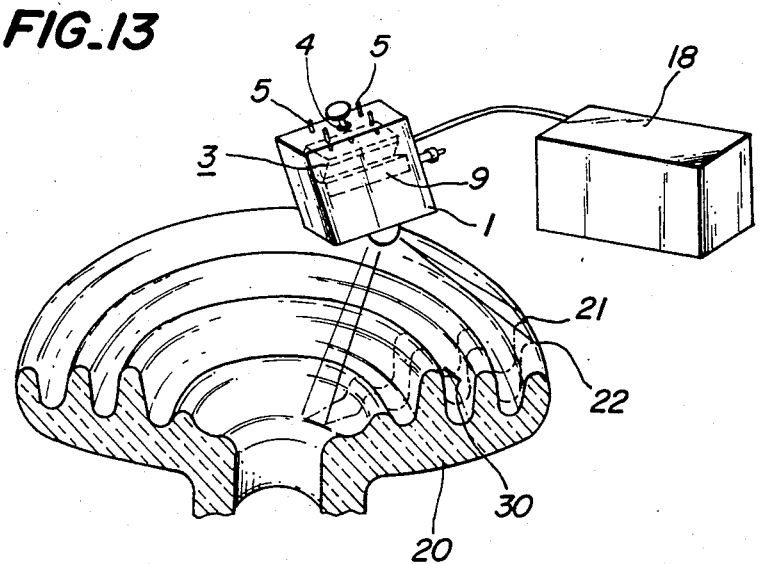
FIG. 13 is a perspective view partially in cross-section for showing a manner of use of the camera for visual inspection according to the present invention.

The camera of the invention is set over the object 20 such as a suspension insulator as shown in FIG. 13 by making the longitudinal direction of the vertex line 6 of the reflecting mirror 3 to match with the radial direction of the object 20. The object 20 is rotated and the reflected light from the surface of the insulator is received by the lens 2. The incident light from the lens 2 is splitted into two portions by the two symmetrical reflecting surfaces 7 and 8 arranged to incline equiangularly with respect to the optic axis 1 with the vertex line 6 being normal to the optic axis 1. The splitted light beams are received by the linear image sensing devices 9 and 10 being arranged at the two separate positions on the inner surface of the camera body 1 on which the respective reflected light falls on. The received lights are modified into electric signals representing luminance variation along the radial direction and are processed in the processor 18. As can be understood from FIGS. 1 and 3, light beams along paths slightly deviated in either right or left from the optic axis 1 are reflected by the reflecting surface 7 or 8 towards the linear image sensing device 9 or 10. According to the present invention, the splitting of the light beams having very minor deviation angle from the optic axis is effected by the reflecting mirror 3. Accordingly, it becomes possible that the linear image sensing devices 9 and 10 need not be arranged very closely each other as in the case of the conventional devices. The brightness of two close lines 21 and 22 on the object 20 can clearly be observed and are converted into two electric signals by the linear image sensing devices 9 and 10. By arranging the reflecting mirror 3 freely to move along the optic axis 1, the interval of such comparing lines 21 and 22 on the surface of the object 20 can be varied in a certain limited range. This is by a reason that by advancing the reflecting mirror 3 towards the object 20, the light paths incident on the linear image sensing devices 9 and 10 become apart from the optic axis 1 and contrary thereto if the reflecting mirror 3 is retracted, light beams on the light paths of more closing to the optic axis may become incident to the linear image sensing devices 9 and 10.

Figure 14:
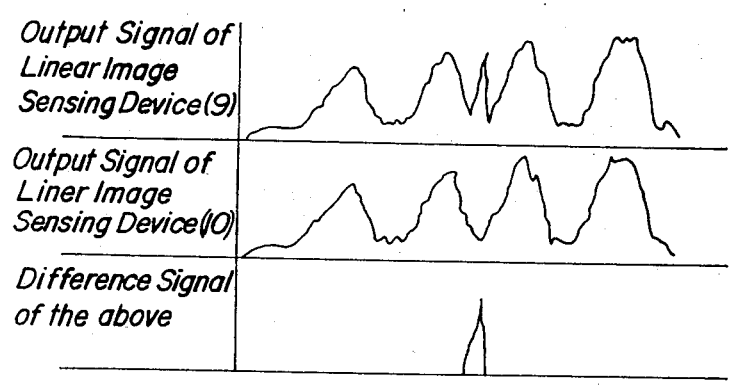
FIG. 14 is a waveform diagram for showing the output signals and the difference signal of respective image sensing devices.

The two output signals from the linear image sensing devices 9 and 10 may vary in the radial direction of the object, but the output signals from the corresponding sensor elements on the respective linear image sensing devices 9 and 10 are identical when no defect exists. Therefore, if we obtain a difference between the output signal from the linear image sensing device 9 and that from the linear image sensing device 10, the processed difference signal in such a case will have value zero. On the contrary, if there is a defect 30 on the surface of the object 20 as shown in FIG. 13, the output signal of the linear image sensing device 9 representing the image on the line 21 will be a waveform including a brightness variation as shown on the top line of FIG. 14 and the output signal of the linear image sensing device 10 representing the image on the line 22 will be a waveform as shown in the 2nd line of FIG. 14. Accordingly, by obtaining the difference between the two signals, only a signal representing the defect as shown in the bottom line of FIG. 14 can be derived. Moreover, the interval between the two lines 21 and 22 to be compared can be made very closely so that even a very small defect 30 can be identified and the inspection accuracy can remarkably be higher than the conventional system. Instead of using the reflecting mirror 3, it is possible to use an image guide consisting of optical fibers having two splitted top to guide the lights to the linear image sensing devices. But due to complication of the construction, the use of the reflecting mirror 3 as in the case of present embodiment of the invention is preferred by practical reasons.

In the camera for the visual inspection made according to the present invention, it is required that the images of two adjacent points on the surface of the object 20 are accurately focused on the corresponding sensor elements arranged on both the two linear image sensing devices. However, the linear image sensing devices are individually attached on separate locations on the inner side of the camera body 1, achieving the alignment of such devices may sometime be difficult. In more detail, a sensor element has a size of only some 10 $\mu$m so that if there is a deviation of the arrangement of about 10 $\mu$m along the direction of array of the sensor elements of the linear image sensing devices 9 and 10, the devices may produce a defect signal due to variation of illumination by the brightness deviation despite the fact that there is no defect on the surface of the object 20. In the present invention, there is provided a fine adjustment mechanism at least at one of the linear image sensing devices 9 and 10, the aforementioned deviation of mounting position of the linear image sensing device 9 or 10 may be compensated by moving the one of the devices, for instance, the sensing device 9 in the direction of array of the sensor elements in an accuracy of order of about 10 $\mu$m. By this arrangement, the possible deterioration of nspection accuracy by the manner of arrangement of the linear image sensing devices 9 and 10 on the separated locations of the camera body 1 can be prevented.

Furthermore, by using incident light adjusting filter 24 having the darkness variation corresponding to the variation pattern of sensitivity characteristics of the sensor elements along the direction of the array as seen from FIGS. 10 to 12, both the linear image sensing devices may have uniform apparent sensitivity characteristics along the whole length thereof. By this the deterioration of inspection accuracy due to the difference of the sensitivity characteristics between the linear image sensing devices 9 and 10 can completely be avoided.

Figure 16:
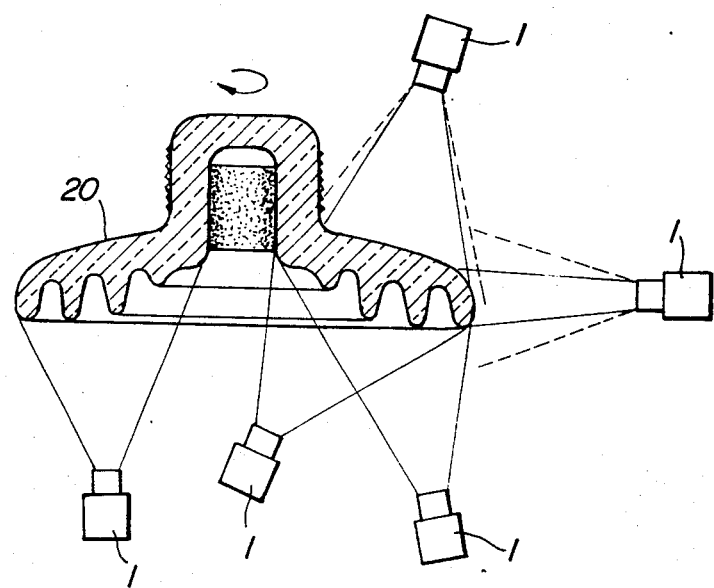
FIG. 16 is a cross-sectional view for showing the manner of use of the device of the present invention.

In the practical suspension insulator inspection in the manufacturing line, a plurality of this kind of cameras are used for the inspection of the whole surface of the insulators as shown in FIG. 16. In order to make the magnification of the number of cameras identical, the distance between the cameras and the object 20 must be made substantially constant. In this case portions other than the required inspection surface may also fall in the field of view of the camera so that unwanted spurious noise waveforms are induced at both extremities of the two linear image sensing devices as can be seen from FIG. 17. Such unwanted spurious noises 60 may remain even in the difference signal shown in the third line of FIG. 17. In the present invention, the pair of shielding plates 15A, 15A or 15B, 15B arranged very closely in front of the linear image sensing device 9 or 10 may be adjusted to move in the direction of the array of the sensor elements by means of the driving screw 16 and the field of view of each camera is limited to prevent the incidence of lights coming other than the required inspection surface as shown by the full line in FIG. 16. By this adjustment, the noise waveform will not be produced in each of the linear image sensing devices 9 and 10 and only the wanted difference signal 50 can be derived as shown in FIG. 17 line (D). The adjustment of the field of view can be effected at each one of the cameras so that both the wide field of view and the narrow field of view can be inspected by using just one kind of the camera.

Effect of the Invention

According to the present invention, as can be understood clearly from the foregoing explanation, brightness of two closely located lines on the surface of the object can be compared after converting them into electric signals by using the linear image sensing devices known per se. The interval of the two lines to be compared may be adjusted freely so that a defect on the surface of an object can be accurately inspected by a suitable choice of such interval depending upon the nature of the object. Furthermore, a fine adjustment mechanism in the direction of the array of the sensor elements is provided at least for one of the linear image sensing devices, the deterioration of inspection accuracy due to provision of the linear image sensing devices at locations separated from each other can be avoided. By the provision of light amount adjusting filter having darkness distribution matching with the sensitivity characteristics in the direction of the array of the sensor elements at front of the linear image sensing device, the deterioraton of accuracy of inspection due to the difference of the two linear image sensing devices can successfully be avoided. Furthermore, by the provision of shielding plates movable in the direction of array of the sensor elements at front of and at very proximity of the linear image sensing device, the field of view of each camera can freely be adjusted to limit to the required field of view only. By this, the noise waveform due to the incidence of light from portions other than the desired inspecting surface may be shielded while keeping the magnification of the cameras as constant thus the spurious noise waveform can successfully be eliminated.

According to the present invention, defects on the whole surface of an object can be inspected by using a same kind of cameras without affecting the inspection accuracy so that the invention is particularly useful to the cameras for the visual inspection for accurately inspecting the presence of defects on an object having a complicated rugged outer configuration such as insulators or the like in an on-line inspecting system.

The invention has been turned out particularly useful in practice.

What is claimed is:

1. A camera for visual inspection for defects having a camera body equipped with a lens having an optic axis, the improvement comprising: a reflecting mirror having two symmetrical reflecting surfaces extending equiangularly with respect to said optic axis and forming a vertex line therebetween, the vertex line extending normal to the optic axis, and two linear image sensing devices mounted on inner surface of the camera body at two separate points to receive light passing through said lens and reflected by said two reflecting surfaces.

2. A camera for visual inspection as claimed in claim 1, wherein the reflecting mirror is arranged to freely move back and forth along the optic axis.

3. A camera for visual inspection as claimed in claim 1, wherein at least one of the linear image sensing devices is provided with a fine adjustment mechanism for finely adjusting its mounting position along the direction of array of sensor elements.

4. A camera for visual inspection as claimed in claim 1, wherein at least one of the linear image sensing devices is provided with a light amount adjusting filter having darkness distribution to match with a pattern of variation of sensitivity characteristics along the direction of array of sensor elements of the linear image sensing device to compensate the variation.

5. A camera for visual inspection as claimed in claim 1, wherein each of the linear image sensing devices is provided with shielding plates being movable along the direction of the array of the sensor elements in front of and in very close proximity thereto.

* * * * *